(12) United States Patent
Goswami et al.

(10) Patent No.: US 6,638,546 B2
(45) Date of Patent: Oct. 28, 2003

(54) BIOACTIVITY OF METHYL PALMITATE OBTAINED FROM A MANGROVE PLANT SALVADORA PERSICA L

(75) Inventors: Usha Goswami, Goa (IN); Nazarine Fernandes, Goa (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 10/179,307

(22) Filed: Jun. 26, 2002

(65) Prior Publication Data

US 2003/0012832 A1 Jan. 16, 2003

Related U.S. Application Data

(63) Continuation of application No. 09/818,791, filed on Mar. 28, 2001, now abandoned.

(51) Int. Cl.⁷ ............................................. A61K 35/78
(52) U.S. Cl. ...................................... 424/769; 424/725
(58) Field of Search ................................ 424/725, 769

(56) References Cited

U.S. PATENT DOCUMENTS

| | | |
|---|---|---|
| 4,927,629 A | 5/1990 | Bing |
| 5,109,022 A | 4/1992 | Jeanne et al. |
| 5,821,249 A | 10/1998 | Wood et al. |
| 6,039,950 A | 3/2000 | Khwaja et al. |
| 6,049,013 A | 4/2000 | Ueoka et al. |
| 6,428,823 B1 | 8/2002 | Goswami et al. |

FOREIGN PATENT DOCUMENTS

| | | |
|---|---|---|
| DE | 41 36 811 A1 | 5/1993 |
| WO | WO 97/16192 | 5/1997 |

OTHER PUBLICATIONS

Birdsall, et al., "Muscarinic receptor subclasses", Trends Pharmacological Sciences, vol. 4, pp. 459–461 (1993).
Goodman & Gilman: In: The Pharmacological Basis Of Therapeutics, 9th Ed., pp. 278–279 (1997).
Mortelmans, et al., "Salmonella Mutagenicity Tests: II. Results From the Testing of 270 Chemicals", Environmental Mutagenesis, vol. 8, pp. 1–119 (1986).
Sulaiman, et al., "Effects of Salvadora Persica Extracts on Mice Exploratory Locomotion Activities", J. Ethnopharmacology, 17(3):263–8 (1986). Abstract.
Galati, et al., "Salvadora Persica L: Hypolipidemic Activity on Experimental Hypercholseterolemia in Rat", Phytomedicine, 6(3):181–185 (1999). Abstract.
Khan, et al., "Fatty Acids of Indigenous Resources for Possible Industrial Applications IV, Species of Salvadora Family", Pak. J. Sci. Ind. Res., 15(6):402–4 (1972). Abstract.

*Primary Examiner*—Leon B. Lankford, Jr.
*Assistant Examiner*—Ruth A. Davis
(74) *Attorney, Agent, or Firm*—Piper Rudnick LLP; Steven B. Kelber (57) ABSTRACT

The invention discloses a process of extracting, fractionating and purifying bioactive molecules from an associated mangrove plant, methods of screening for pharmacological activities of crude extract, its fractions and purified compounds and use of methyl palmitate obtained from the crude extract as a muscurine antagonist.

8 Claims, 8 Drawing Sheets

BIOACTIVITY OF METHYL PALMITATE OBTAINED FROM A MANGROVE PLANT SALVADORA PERSICA L

This application is a continuation of U.S. application Ser. No. 09/818,791 filed Mar. 28, 2001 now abandoned, allowed, the contents of which are incorporated herein by reference.

FIELD OF INVENTION

The present invention relates to a novel muscurine antagonist obtained from an associated mangrove plant called *Salvadora persica* Linneaus 1753 collected from estuarine mangrove swamps of Goa, India. Particularly, the present invention relates to the use of methyl palmitate isolated from the plant *Salvadora persica* as a muscurine antagonist.

BACKGROUND OF THE INVENTION

Methyl palmitate is a fatty acid methyl ester. It is prepared commercially from naturally occurring edible fats and oils. These compounds are widely used indirectly in a wide range of food, pharmaceutical, cosmetic and industrial applications (Pearson, R., Report of the FAME (Fatty Acid Methyl Esters) Task Force, Jan. 9, 1997). In the same report, data on methyl esters including methyl palmitate, which were tested for oral toxicity in rats, is given. Methyl palmitate was proved to be nontoxic. The report also described that administration of an emulsion of methyl palmitate to mice by oral intubation or intraperitoneal injection produced no alteration in organ weight or phagocytic function of the reticuoendothelial system. In Environment Mutagen 8(Suppl 7):1–119 (1986) (quoted from Pearson, R., supra), it was reported that methyl palmitate was devoid of any mutagenic effect based on the tests on Salmonella and mammalian microsome assays. The methyl palmitate though showed sensitivity of rabbit's skin to the compound, the results with human skin proved to have a very mild effect. Methyl esters of fatty acids can be used as supplementary source of fat for animal feeds.

"Muscarinic actions" are the actions produced as a result of acetylcholine released from the post-ganglionic parasympathetic nerve endings or the actions resulting from exogenously administered acetylcholine on the receptors of organs with post-ganglionic parasympathetic nerve supply. The muscarinic actions of both endogenously released, as well as exogenously administered, acetylcholine are blocked by atropine. The designation "muscarinic actions" comes from the fact that these actions are similar to those produced by the poisonous mushroom alkaloid muscarine (R. S. Satoskar and S. D. Bhandarkar, Pharmacology and pharmacotherapeutics, Vol.1., Popular Prakashan, Bombay (1990).

Acetylcholine acts on two types of receptors, namely muscarinic and nicotinic (Goodman & Gilman's: The Pharmacological Basis of Therapeutics, $9^{th}$ edition, McGraw-Hill Health Professions Division, N.Y.; pp. 278–279 (1997)). Since the activity of the crude extract of the *Salvadora persica* plant was seen on smooth muscle, only muscarinic receptors have been studied (Nazarine, F., Ph.D. Thesis, Goa University, 1998).

A large number of binding and functional studies have indicated the existence of 5 subtypes of muscarinic receptors namely, $M_1$, $M_2$, $M_3$, M4 and $M_5$ (N. J. M. Birdsall and F. C. Hulme, *Trends In Pharmacological Sciences*, 4:459–461 (1983)). The most important are the $M_1$, $M_2$ and $M_3$ muscarinic receptor subtypes. $M_1$ receptors are found in the stomach and mediate gastric secretions, whereas $M_2$ receptors are found in the myocardium of the heart and $M_3$ are found in the ileum and bladder detrusor muscles and cause smooth muscle contractions.

Thompson et al., in PCT Patent Application No. WO 97/16192, published on May 9, 1997, disclose the antimuscarinic activity of derivatives of piperdin and describe their use in the treatment and/or prevention of myopia, commonly known as near-sightedness.

Haertel et al., in DE Patent No. 4136811 published on May 13, 1993, disclose a skin cleanser especially for removing paint containing methyl, ethyl and/or isopropyl palmitate with some solvents and emulsifiers. Jeanne et al., in U.S. Pat. No. 5,109,022, issued on Apr. 28, 1992, describe a composition which contains methyl palmitate and some other compounds and is useful for repelling flying, biting and stinging insects. U.S. Pat. No. 6,039,950, issued on Mar. 21, 2000, describes formulations of several pharmaceutical grade compounds including fatty esters from the Saw Palmetto, which is a small palm found in the southern United States. U.S. Pat. No. 6,049,013, issued on Apr., 11, 2000, discloses that in methods of producing alcohols, the fatty acids (one example is of methyl palmitate) could be extracted from coconut, palm and palm kernel for this use.

U.S. Pat. No. 5,821,249, which issued on Oct. 13, 1998, describes production of anhydroecgonine methylester (MEG) by heating cocaine base ("crack") and their use as anticholinergic agents. MEG alone and in combination with cocaine was tested for action on isolated tracheal rings stimulated to contact with acetylcholine.

There is no patent available on the antimuscarinic activity of methyl palmitate. The present invention for the first time discloses the effect of methyl palmitate on $M_1$ receptors by observing gastric acidity by pyloric ligation under basal conditions. Like atropine, the compound methyl palmitate decreased free acidity. However, in the studies conducted, it was 50 times less potent than the standard antagonist atropine. $M_2$ muscarinic receptors found in the conducting tissue and the myocardium of the heart mediate both the bradycardia and the negative inotropic effect of cholinergic stimulation. The present invention relates to the comparative effect of methyl palmitate and atropine on the rate and force of contraction of the guinea pig atria. It describes the inhibitory effect of atropine. The invention describes that the compound methyl palmitate had no such effect in the dosage range used showing that it probably does not block $M_2$ receptors. Though the reason for this effect is not known yet, the present invention for the first time describes the ability of the compound methyl palmitate to distinguish between the muscarinic receptors in the atrium and elsewhere in the body. The very reason that methyl palmitate does not affect the $M_2$ receptors of the atrium confirms the heterogeneity of muscarinic receptors.

As used herein the term "antimuscarinic activity" means the antagonistic activity on muscarinic receptors, where "antagonistic activity" refers to the inhibitory effect of atropine and the said compound. The "heterogeneity of muscarinic receptors" means the ability of the said compound to distinguish between the muscarinic receptors in the atrium and elsewhere in the body. The "selectivity of the compound" means its inhibitory action only on $M_1$ and $M_3$ muscarinic receptors. The "competitive antagonism" means the compound produced a shift to the right in the dose response curves of the acetylcholine with the maximum response remaining the same. In gastric acidity experiments, the compound was injected subcutaneously as per the body weight of the rat measured in kilograms and written as Kg. s.c. where "s.c." means subcutaneous.

The approach adopted for antagonistic activity screening by pharmacological methods is described for the first time for this compound. The invention describes that methyl palmitate produces a shift to the right in the dose response curves of acetylcholine with the maximal response remaining the same. It further discloses that the competitive antagonism shown by the said compound is reversible in nature. Methyl palmitate blocks $M_3$ receptors in the same way as atropine, though it is 2.2 times less potent.

OBJECTS OF THE INVENTION

The main object of the present invention is to study the compound methyl palmitate purified from the extract of the plant *Salvadora persica* for its antimuscarinic activity.

Another object of the present invention is to study the heterogeneity of methyl palmitate as a muscarinic receptor.

Still another object of the present invention is to study the comparative effect of methyl palmitate and atropine during in vivo and in vitro experiments.

One more object of the present invention is to detect the effect of methyl palmitate on the dose response curve of acetylcholine.

One other object of the present invention is to detect the effect of methyl palmitate in rats.

Another object of the present invention is to find out the effect of the methyl palmitate in guinea pigs.

SUMMARY OF THE INVENTION

The present invention seeks to overcome the drawbacks inherent in the prior art by providing highly efficient and selective methods for screening antimuscarinic activity of a methyl palmitate compound purified from the plant *Salvadora persica* and discloses the use of this compound as a muscurine antagonist.

DETAILED DESCRIPTION OF THE INVENTION

Accordingly, the present invention provides a process for obtaining methyl palmitate from a mangrove plant source, namely *Salvadora persica*, said process comprising:
   (i) obtaining an extract from *Salvadora persica* and
   (ii) extracting and purifying the biologically active extract to obtain methyl palmitate from the extract.

Also, the present invention provides a process for preparation of the extract comprising methyl palmitate from the mangrove plant source *Salvadora persica*, said process comprising:
   (i) air-drying the plant parts;
   (ii) immersing the plant parts in 90 percent aqueous methanol for one week at room temperature (28±2° C.) to obtain a methanolic extract;
   (iii) filtering the methanolic extract by conventional methods; and
   (iv) evaporating the methalonic extract at room temperature (28±2° C.) to obtain a crude extract.

More particularly, the present invention provides a process for the extraction and purification of a biologically active methyl palmitate, useful as a muscarine antagonist, from an extract of *Salvadora persica* mangrove plant, said process comprising:
   a) obtaining a solvent extract from the plant parts of *Salvadora persica*,
   b) testing the extract using methods of pharmacology;
   c) fractionating the extract into fractions;
   d) testing the fractions using methods of pharmacology;
   e) isolating a pure compound by a conventional method;
   f) testing the pure compound by using methods of pharmacology; and
   g) identifying the compound by conventional methods.

In an embodiment of the present invention, the plant parts of *Salvadora persica* are selected from leaves, stems and flowers.

In another embodiment of the present invention, the extract is obtained using solvents such as chloroform and hexane.

In yet another embodiment of the present invention, the methyl palmitate molecule is characterized by:
   Molecular formula: $C_{16}H_{32}O_2$
   Molecular weight: 256
   Melting point: 30° C.

As used herein, the term "extract" denotes the extract obtained from the plant *Salvadora persica*.

In still another embodiment of the present invention, methyl palmitate is capable of distinguishing between muscarinic receptors of atrium and other parts of the body and shows heterogeneity of muscarinic receptors. Methyl palmitate shows competitive antagonism, which is reversible in nature.

In one other embodiment of the present invention, the methyl palmitate obtained inhibits gastric acidity and gastrointestinal disorders. The applicants have found that methyl palmitate inhibits gastric acidity as it exhibits activity on the $M_1$ receptors found in the stomachs of rats. It also exhibits activity against $M_3$ receptors found in the ileal and bladder detrusor muscles of pig.

It has also been found that methyl palmitate does not block $M_2$ receptors and thereby does not have inhibitory effect on the contractions of atrial muscles of guinea pig in the dosage range used.

In still another embodiment of the present invention, methyl palmitate produces a right shift in the dosage response curves of acetylcholine with the maximum response remaining the same.

In one more embodiment of the present invention, methyl palmitate shows muscarinic activity with a milder potency than atropine.

Based on the studies conducted, the invention provides a novel muscurine antagonist obtained from the plant *Salvadora persica*. The applicants have found that the extract, as well as methyl palmitate obtained from the extract of *Salvadora persica*, acts as a muscurine antagonist.

Additionally, the invention provides pharmaceutical compositions useful as muscarine antagonists, comprising an effective amount of extract obtained from the mangrove plant *Salvadora persica*, optionally with conventional additives. The composition may also contain methyl palmitate as the active ingredient. The amount of the active ingredient in the composition may be readily determined by a person skilled in the art depending on factors such as the patient being treated, his body weight, etc. Generally, the effective amount may be in the range of 0.1 to 10 mg/kg body weight.

Further, the applicants have found that the compound methyl palmitate obtained from the plant has the general capacity to impact muscle contractions by slowing down or halting contractions. As a result, it is capable of reducing spasms in smooth muscles, hence acting as an antimuscuranic agent. Thus, the compound acts as an effective "muscurine antagonist." Preferably, the method of treatment comprises the step of administering a composition containing the compound methyl palmitate obtained from *Salvadora persica* to a subject in need thereof. The diseases for which the composition may be administered are renal colics, bronchial asthma, abdominal cramps, motion sickness and prevention of premature delivery. The applicants believe that the compound methyl palmitate in the extract is responsible for the above activities.

In an embodiment of the present invention, the dose response curves of the standard agonistic drug acetylcholine were carried out in the absence and presence of methyl palmitate on guinea pig atria for the said activity on $M_2$ and $M_3$ receptors.

In another embodiment of the present invention, for the purpose of comparison, three doses of atropine were used for testing antimuscarinic activity on $M_3$ receptors on ileal and bladder muscles, and the amounts of the doses were:

$35 \times 10^{-6}$ moles/ml of bath concentration;

$86 \times 10^{-6}$ moles/ml of bath concentration; and $173 \times 10^{-6}$ moles/ml of bath concentration.

In yet another embodiment of the present invention, for comparative purposes, three doses of atropine were administered on $M_2$ receptors and the amounts of the doses were:

$0.4 \times 10^{-6}$ moles/ml of bath concentration;

$0.9 \times 10^{-6}$ moles/ml of bath concentration;

$1.7 \times 10^{-6}$ moles/ml of bath concentration.

In still another embodiment of the present invention, for comparative purposes, three doses of atropine were administered to $M_1$ receptor for testing gastric acidity:

0.01 mg/kg of the body weight of rat;

0.05 mg/kg of the body weight of rat; and 0.10 mg/kg of the body weight of rat.

In another embodiment, the percent inhibition of gastric acidity by the compound methyl palmitate was:

50.72% when the dose was 1 mg/kg of the body weight of rat;

55% when the dose was 3 mg/kg of the body weight of rat; and 91.5% when the dose was 5 mg/kg of the body weight of rat.

Description of the Tables

Table 1: Effect of methyl palmitate and atropine on gastric acidity in rats.

ADVANTAGES OF THE INVENTION

The invention pertains to a new muscarinic antagonist purified from a novel source of an associated mangrove plant. This invention can be utilized for adopting the methods of pharmacological screening of bioactive molecules for antimuscarinic activity in both in vivo and in vitro experiments. The comparative effect of methyl palmitate and atropine on $M_1$, $M_2$, and $M_3$ receptors discloses the inhibitory effect of methyl palmitate on $M_1$ and $M_3$, whereas atropine has inhibitory effect on all the three receptors. The present invention also contemplates that the compound methyl palmitate had no such effect in the dosage range used, showing that it probably does not block $M_2$ receptors.

This ability of the methyl palmitate in distinguishing muscarinic receptors can have a wider applied aspect in making pharmaceutical compositions for clinical testing of selective tissue remedies.

Thus, in a preferred mode of use, the finding that the methyl palmitate produces a shift to the right in the dose response curves of acetylcholine with the maximal response curves of acetylcholine remaining the same.

The present invention also contemplates the finding that the antagonism is competitive as shown by the said compound. Methyl palmitate blocks $M_3$ receptors in the same way as atropine, though it is 2.2 times less potent. The selectivity and lower potency characteristic of a compound together can make a good combination in testing compositions to have an added advantage of overcoming side effects on unrelated tissues and/or organs.

In a preferred mode of use, the compound methyl palmitate can be a potential inhibitor of gastric acidity and gastrointestinal disorders. The percent inhibition of gastric acidity was directly proportional to the dose of the said compound.

EXAMPLE 1

Chemicals, Reagents, Apparatus Used and Their Sources

| Name of reagents/chemicals/glassware | Company |
| --- | --- |
| Acetylcholine chloride | Hopkins & Williams Ltd. |
| Atropine | SIGMA |
| Chloroform | S.d.fine chemicals |
| Ether | S.d.fine chemicals |
| Saline | Glaxo |
| Burette | Borosil |

Apparatus

1. Physiograph
    Co.: Biodevices
    Ambala, India.
2. Force Transducer
    Model No. T-305
    Co.: GRASS
    USA.
3. Organ Bath
    Ambala, India.

The methods of screening and the results of antimuscarinic activity of methyl palmitate, an aliphatic ester extracted and purified from an associated mangrove plant identified as *Salvadora persica*, are disclosed.

EXAMPLE 2

Collection of Mangrove Plants

Mangrove plants *Salvadora persica* L were collected from the coast of Goa along Ribandar, near the mouth of the Mandovi estuary, upstream. This species is ubiquitous to the coastal areas of Goa and was collected manually from the intertidal banks.

EXAMPLE 3

Processing

The collected mangrove plants were washed first with seawater followed by tap water. The undesired materials were sifted out while washing with tap water to get rid of the salts. The leaves, stems, and flowers of the associated mangrove plant were air dried. After drying, the plant material was cut into small pieces and immersed in the solvent (90% aqueous methanol) for a week for extraction. Care was taken that these were properly soaked/dipped in the solvent so as to check putrefaction.

EXAMPLE 4

Preparation of Crude Extract

Extraction and preparation of crude extract was carried out by a cold percolation method at room temperature and by solvent evaporation in a water bath (temperature 50° C.) under reduced pressure. This helps in protection of any heat labile metabolite present in it. Re-extraction was done twice until the extract was concentrated under vacuum to obtain the crude extract.

EXAMPLE 5

Fractionation of the Crude Extract

The crude extract was partitioned into petroleum ether, chloroform, n-butanol and aqueous fractions using a separating funnel. Petroleum ether was added to the extract in the separating funnel and separated out. Next, chloroform was added to the residue, mixed well and the lower layer separated. To the residue, butanol was added and the top layer represented the butanol fraction and lower layer the aqueous fraction. Extraction of each fraction was done thrice and, whenever there was emulsion, sodium chloride was added for breaking the emulsion. Sodium sulphate was added to the chloroform and butanol fractions to remove traces of water before concentration. All the fractions were concentrated in the same manner as the crude extract. These fractions were tested for the same pharmacological activity as the parent crude extract.

Pharmacological Testing of Crude Extract

Female, virgin, guinea pigs weighing around 300 to 350 g, housed under uniform husbandry conditions (temperature 25±1° C.) were used. The animals were starved 24 hours prior to the experiment, only water was provided adlibitum. The isolated guinea pig ileum was used to study the antispasmodic anticholinergic oxytocic and tocolytic activity. All physiological solutions were prepared fresh at the time of the experiment.

EXAMPLE 6

Pharmacological Testing

For pharmacological testing on guinea pig ileum, the guinea pig was sacrificed by stunning with a sharp blow on its head. The abdomen was quickly cut open. Towards the lower end of the abdomen was the greenish sac-like caecum. The small intestine was marked by a localized thickening in the wall—a Peyer's patch of lymphoid tissue. The lowermost 10 cm of ileum nearest to the ileocaecal junction was discarded. From there, about 10 cm of ileal tissue was cut off and freed of mesentery and placed in a petridish containing warm Tyrode solution. The lumen of the ileum was gently rinsed out using a hypodermic syringe filled with Tyrode solution to prevent accumulation of mucus in the lumen. The ileum was cut into small segments of about 3–4 cms in length in the fully relaxed state. The lower end was sutured to a tissue holder by making a loop first to avoid direct contact with the tube. The tissue was positioned in an organ bath of capacity 10 ml containing tyrode solution aerated with air at 37° C. The thread of the upper end of the ileum was fixed to the lever of a force transducer (FT 03), which measures muscle contractions isometrically, and connected to a Grass Polygraph (Model 7). The ileal tissue was kept to stabilize in Tyrode solution for 30 minutes and the fluid in the organ bath was renewed every 10 minutes.

Two to four doses of spasmogens (acetylcholine, histamine, 5 hydroxytryptamine, barium chloride and nicotine) were added to the bath to obtain uniform amplitude with a contact period of 30 seconds of contraction, which was recorded on the polygraph. The aqueous solutions of the extracts and fractions were added 1 minute before the addition of the spasmogens. The effects of graded doses of the extracts (50×250 µg/ml) on the spasmogen were induced contraction and percent reduction of contractions measured as per the formula given below:

$$\%Inhibition = \frac{X-Y}{X} \times 100$$

wherein X=height of standard contraction (mm).
Y=height of standard contraction in presence of the extract (mm).

EXAMPLE 7

Figure 6:
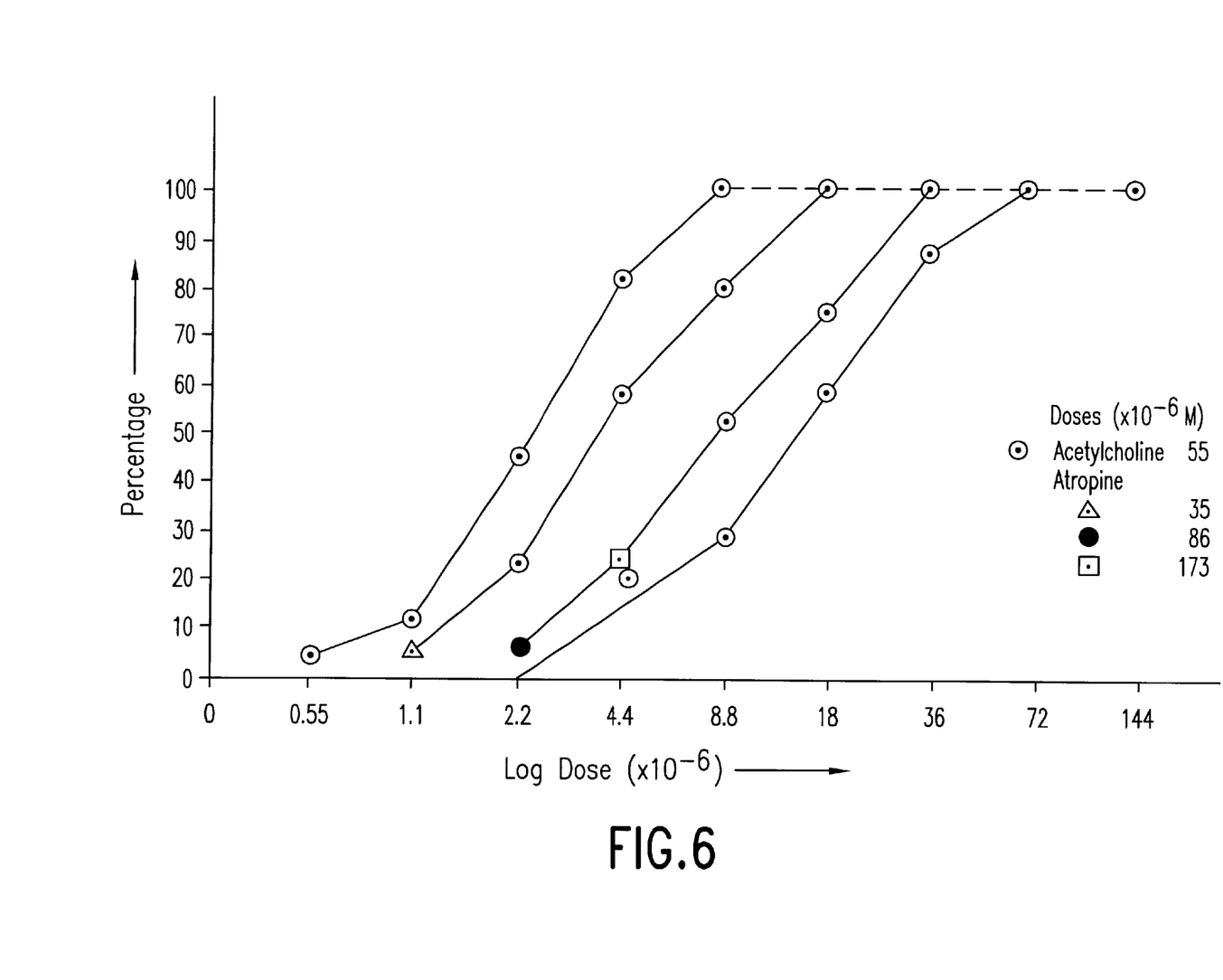
FIG. 6: Dose response curve of acetylcholine on guinea pig ileum in the absence and presence of atropine.

For experiments upon isolated guinea pig uterus, the bicornuate uterus was dissected out and freed of fat tissue. One horn was cut-off and kept in a shallow dish containing a physiological solution, i.e., de Jalon's fluid, which was previously aerated with air. Air was preferred to oxygen as the tissue was thin and saturation was faster. The two ends were sutured. The lower end of the uterine strip was tied to a tissue holder and suspended in an organ bath of 10 ml capacity and the upper end, being more sensitive, to the lever of the force transducer (FT 03) connected to a Grass Polygraph (Model 7) (FIG. 6). It was left to stabilize for 30 minutes, renewing the physiological solution in the bath every 10 minutes. The response of the uterus to different doses of the extract (50×250 µg/ml) against standard uterine stimulants like oxytocin and PG $F_{2\alpha}$ with a contact period of 60 seconds was recorded on the polygraph. The tocolytic effect was evaluated by the formula given below:

$$\%Inhibition = \frac{X-Y}{X} \times 100$$

wherein X=height of standard contraction (mm).
Y=height of standard contraction in presence of the extract (mm).

EXAMPLE 8

Phamacological Testing of Pure Compounds

In vitro experiments: The active fractions were isolated for anticholinergic activity, the five compounds isolated were tested only on isolated guinea pig ileum. The longitudinal ileal muscle from a freshly killed guinea pig was suspended in an organ bath of 10 ml capacity, filled with Tyrode solution and aerated with air. Two or four doses of the standard drug acetylcholine were added to the bath to obtain uniform amplitude with a contact period of 30 seconds, the contractions of which were recorded on a polygraph. The five compounds isolated were tested in doses of 196 and $392 \times 10^{-6}$ moles per ml of bath concentration. The effect of the compounds against acetylcholine were induced contraction and percentage reduction of contractions measured.

EXAMPLE 9

Preparation of Stock Solutions and Various Doses of Methyl Palmitate, Acetylcholine and Atropine Methyl palmitate purified from the chloroform fraction of the crude extract of the said plant was in the powder form. To make its stock solution of 1 mg/ml strength, the weighed powder was first dissolved in a drop of chloroform and then the volume was made to 1 ml by adding distilled water. The stock solution was stored at 4° C. The different concentrations of the doses were prepared by diluting the stock solution with distilled water. Acetylcholine was used as the standard muscarinic drug, while atropine was used as the standard antagonist. Stock solutions of both these standard drugs were prepared and then serially diluted in distilled water to give different concentrations.

EXAMPLE 10

Doses for in vivo Gastric Activity Testing on $M_1$ Receptors

These activities were tested upon rats. The doses of methyl palmitate used were 1 milligram per kilogram of the body weight of rat injected subcutaneously (1 mg/kg s.c), 3 milligrams per kilogram of the body weight of rat (3 mg/kg s.c), and 5 milligrams per kilogram of the body weight of rat (5 mg/kg s.c). For comparative purposes, the doses of atropine used for testing gastric acidity were 0.01 milligram per kilogram of the body weight of rat injected subcutaneously (0.01 mg/kg s.c), 0.05 milligram per kilogram of the body weight of rat injected subcutaneously (0.05 mg/kg s.c), 0.10 milligram per kilogram of the body weight of rat injected subcutaneously (0.10 mg/kg s.c.).

EXAMPLE 11

Doses for in vitro Testing on $M_2$ Receptors of Atrial Tissue

Four doses of methyl palmitate ($20 \times 10^{-6}$ moles per milliliter of bath concentration; $40 \times 10^{-6}$ moles per milliliter of bath concentration; $196 \times 10^{-6}$ moles per milliliter of bath concentration; and $392 \times^{-6}$ moles per milliliter of bath concentration were prepared by diluting the stock solution with distilled water. For comparative purposes, the doses of atropine used were $0.4 \times 10^{-6}$ moles per milliliter of bath concentration; $0.9 \times 10^{-6}$ moles per milliliter of bath concentration and $1.7 \times 10^{-6}$ moles per milliliter of bath concentration.

EXAMPLE 12

Doses of in vitro Testing of $M_3$ Receptors of Ileum and Bladder

The three doses prepared and applied were $98 \times 10^{-6}$ moles per milliliter of bath concentration; $196 \times 10^{-6}$ moles per milliliter of bath concentration and $392 \times 10^{-6}$ moles per milliliter of bath concentration. For comparative purposes, the three doses of atropine used were $35 \times 10^{-6}$ moles per milliliter of bath concentration; $86 \times 10^{-6}$ moles per milliliter of bath concentration and $173 \times 10^{-6}$ six moles per milliliter of bath concentration.

EXAMPLE 13

Administration of Methyl Palmitate for in vivo Experiments

The in vivo experiments for gastric acidity testing were performed by pyloric ligation on rats. Albino rats of either sex weighing 190–250 grams were randomly divided into groups of 6, with a group of 6 rats serving as control. All the rats were starved for 48 hours prior to the experiment. After the first 24 hours, they were given access to 8% sucrose in 0.2% sodium chloride for 8 hours. Water was permitted adlibitum except during the 8 hours of sucrose treatment and 2 hours previous to pyloric ligation.

Basal gastric acidity was determined by pyloric ligation under ether anaesthesia followed by gastric lavage with normal saline. Except for the control group, all the rats received 3 doses (1, 3 & 5 mg/kg) of the said compound and standard antagonist atropine (0.01, 0.05 & 0.1 mg/kg) subcutaneously 15 minutes prior to pyloric ligation. Three hours later the animals were killed and the stomach was tied at the oesophageal junction and removed. The contents were collected by cutting along the greater curvature and the free acidity was determined by titration against 0.01 normal NaOH using Topfers reagent as indicator.

EXAMPLE 14

In vitro Experiments for Testing Antimuscarinic Activity of Methyl Palmitate

The in vitro experiments were performed on atria, ileum and bladder tissues of guinea pig. Atria were removed, and one end was tied to an oxygen tube and the other end was fixed to a Force transducer (Model T-305), which is connected to a physiograph (Biodevices Physiograph). The atria beat spontaneously, and after equilibration (30 minutes), resting tension was adjusted to the peak of the length tension curve followed by a re-equilibration period (30 minutes). Cumulative concentration response curves to acetylcholine were obtained before and after addition of increasing concentrations of the compound (doses said in Example 5). Responses were expressed as a percentage of the maximal inhibition of atrial rate induced by acetylcholine in absence of the antagonist (compound).

The longitudinal ileal muscle was suspended in an organ bath in aerated Tyrode solution. Antagonistic activity was determined from concentration response curves to acetylcholine in the absence or presence of increasing concentrations of the compound and of the muscarinic antagonist atropine. Doses of the compound were as given in Example 5.

The longitudinal bladder detrusor strips were suspended under a resting tension (0.5 g) in aerated Tyrode physiological solution. Tension was measured with an isometric force transducer (FT 305), and responses were recorded on a Biodevices Physiograph. Antimuscarinic activity was determined from concentration response curves to acetylcholine in the absence or presence of increasing concentrations of the said compound. Contractile responses were expressed as a percentage of the maximum contraction elicited by acetylcholine in the absence of the said compound. Doses of methyl palmitate, acetylcholine and atropine were as given in Example 5.

EXAMPLE 15

Gastric Acidity

Figure 1:
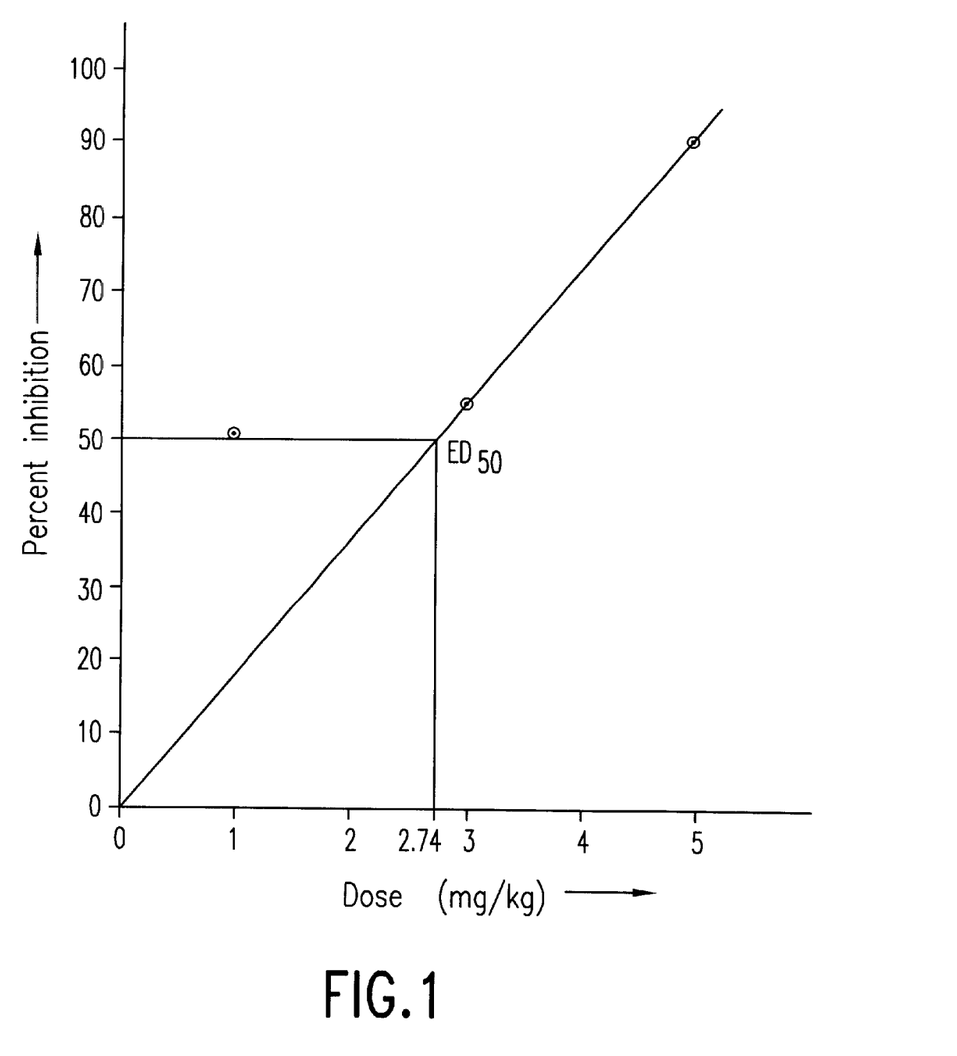
FIG. 1: Percent inhibition in gastric acidity with methyl palmitate.
Figure 2:
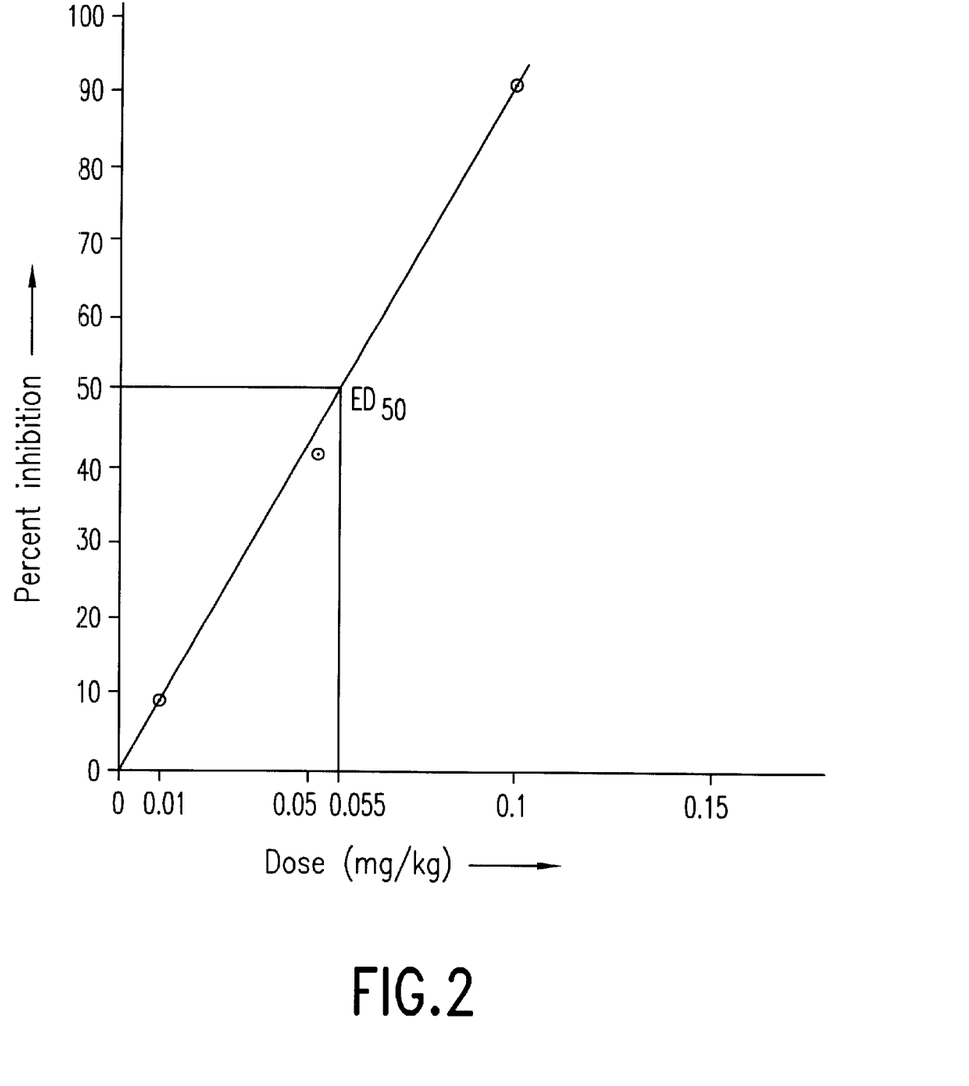
FIG. 2: Percent inhibition in gastric acidity with atropine.

Like atropine, the compound methyl palmitate inhibited basal gastric acidity dose dependently (Table 1) with all three doses (1, 3 & 5 mg/kg s.c.). At the lower dose, inhibition was 50.72%, at 3 mg/kg it was 55.00%, while at the higher dose it was 91.50%, respectively. Here, the compound was fifty times less potent than atropine, as shown in the graphs (FIGS. 1 and 2).

EXAMPLE 16

Effect of Methyl Palmitate on $M_2$ Receptors of the Guinea Pig Atrium

Figure 3:
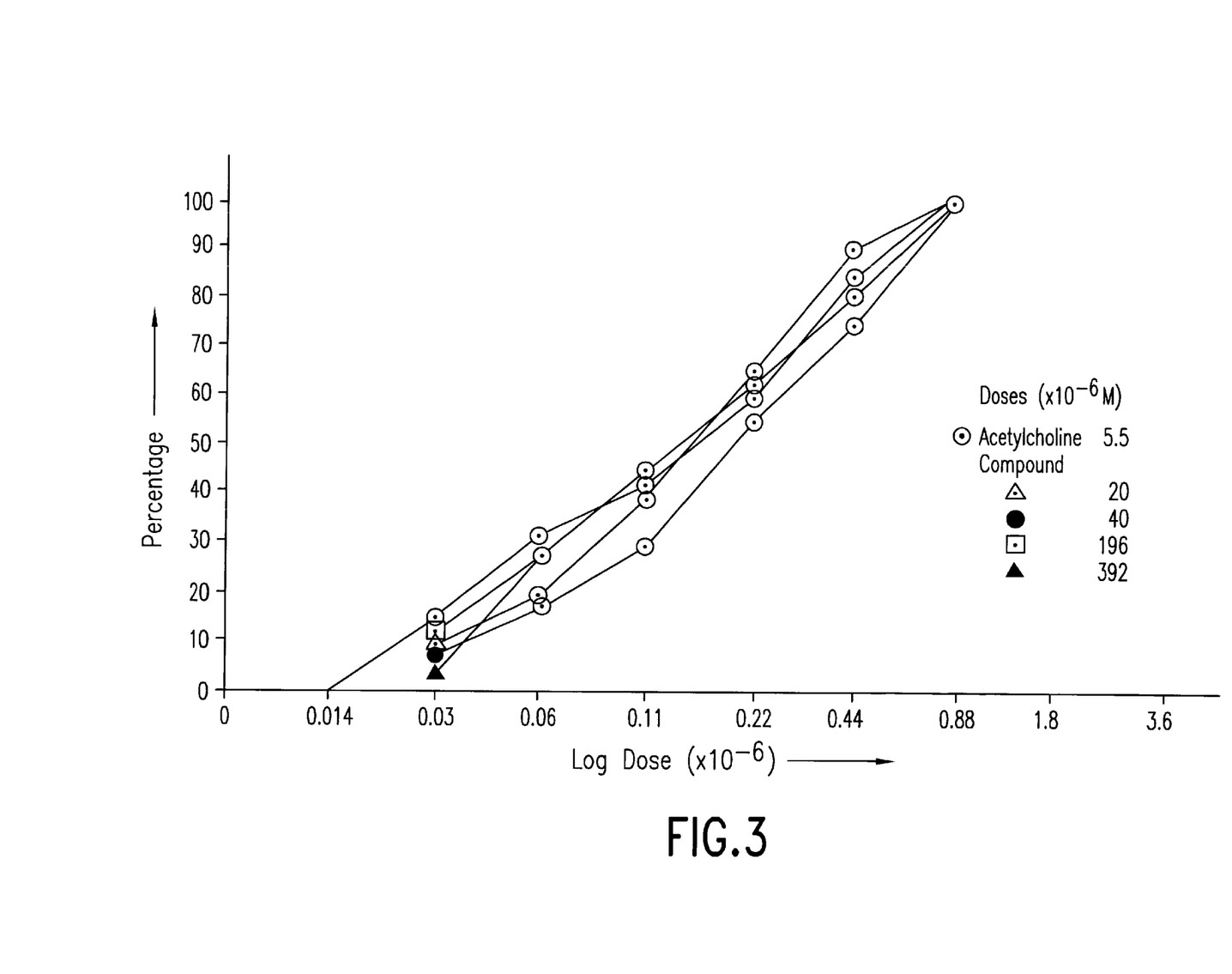
FIG. 3: Dose response curve of acetylcholine on guinea pig atria in the absence and presence of methyl palmitate.
Figure 4:
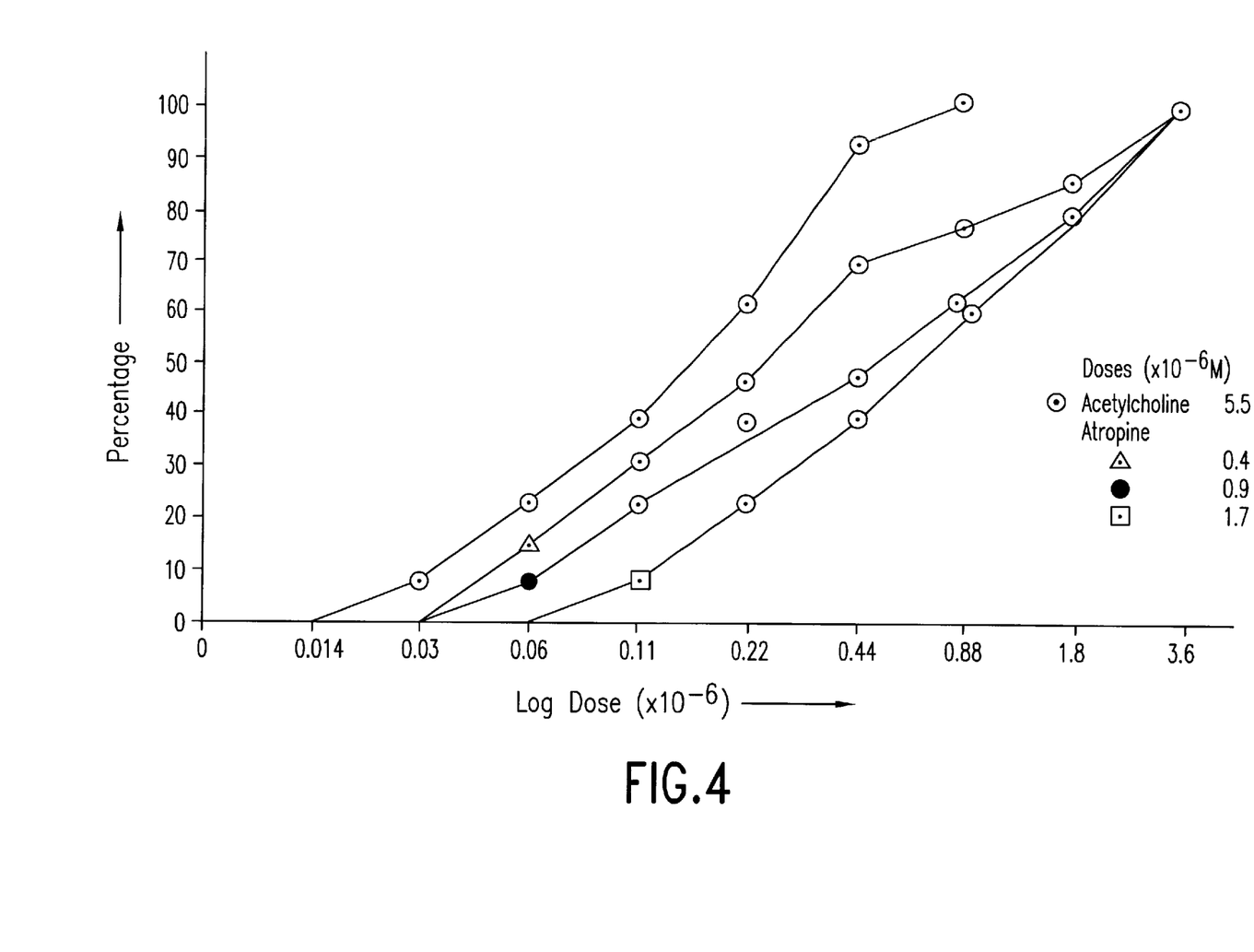
FIG. 4: Dose response curve of acetylcholine on guinea pig atria in the absence and presence of atropine.

The said compound did not produce any positive inotropic or chronotropic effect on its own in the concentrations studied, i.e., $20\times10^{-6}$ moles per ml of bath, $40\times10^{-6}$ moles per ml of bath, $196\times10^{-6}$ moles per ml of bath and $392\times10^{-6}$ moles per ml of bath. The compound methyl palmitate is 118 fold less potent than atropine (FIGS. 3 and 4).

EXAMPLE 17

Figure 5:
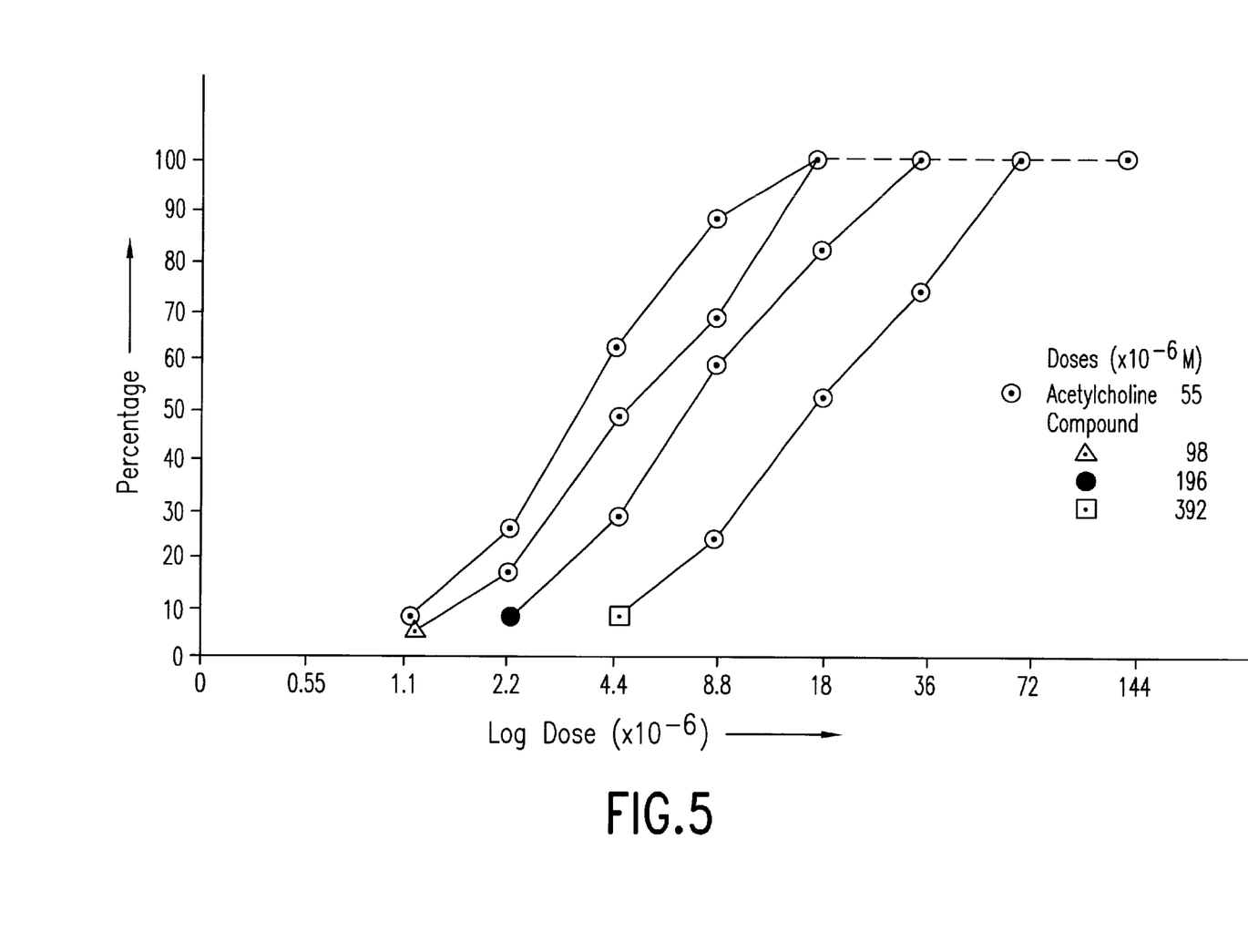
FIG. 5: Dose response curve of acetylcholine on guinea pig ileum in the absence and presence of methyl palmitate.

The compound methyl palmitate in concentrations of $98\times10^{-6}$ moles per ml of bath, $196\times10^{-6}$ moles per ml of bath and $392\times10^{-6}$ moles per ml of bath antagonised contractions of smooth muscle of the ileum produced by the muscarinic agonist acetylcholine. Further, like atropine, this compound produced a shift to the right of the dose response curve to acetylcholine, with no change in the slope and maximum response, suggesting a competitive antagonism (FIGS. 5 and 6). The compound is 2.2 times less potent than atropine.

EXAMPLE 18

Figure 7:
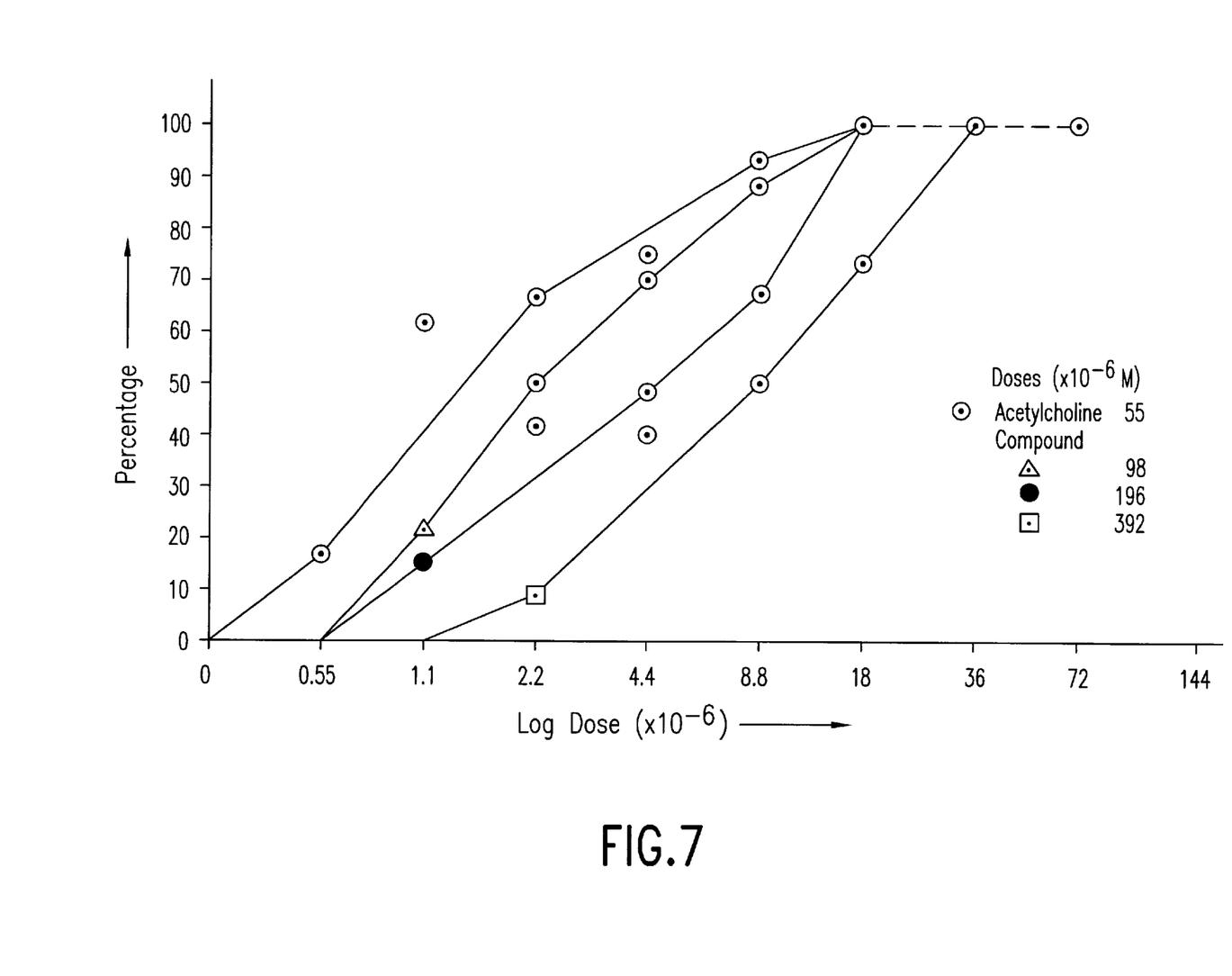
FIG. 7: Dose response curve of acetylcholine on guinea pig bladder in the absence and presence of methyl palmitate.
Figure 8:
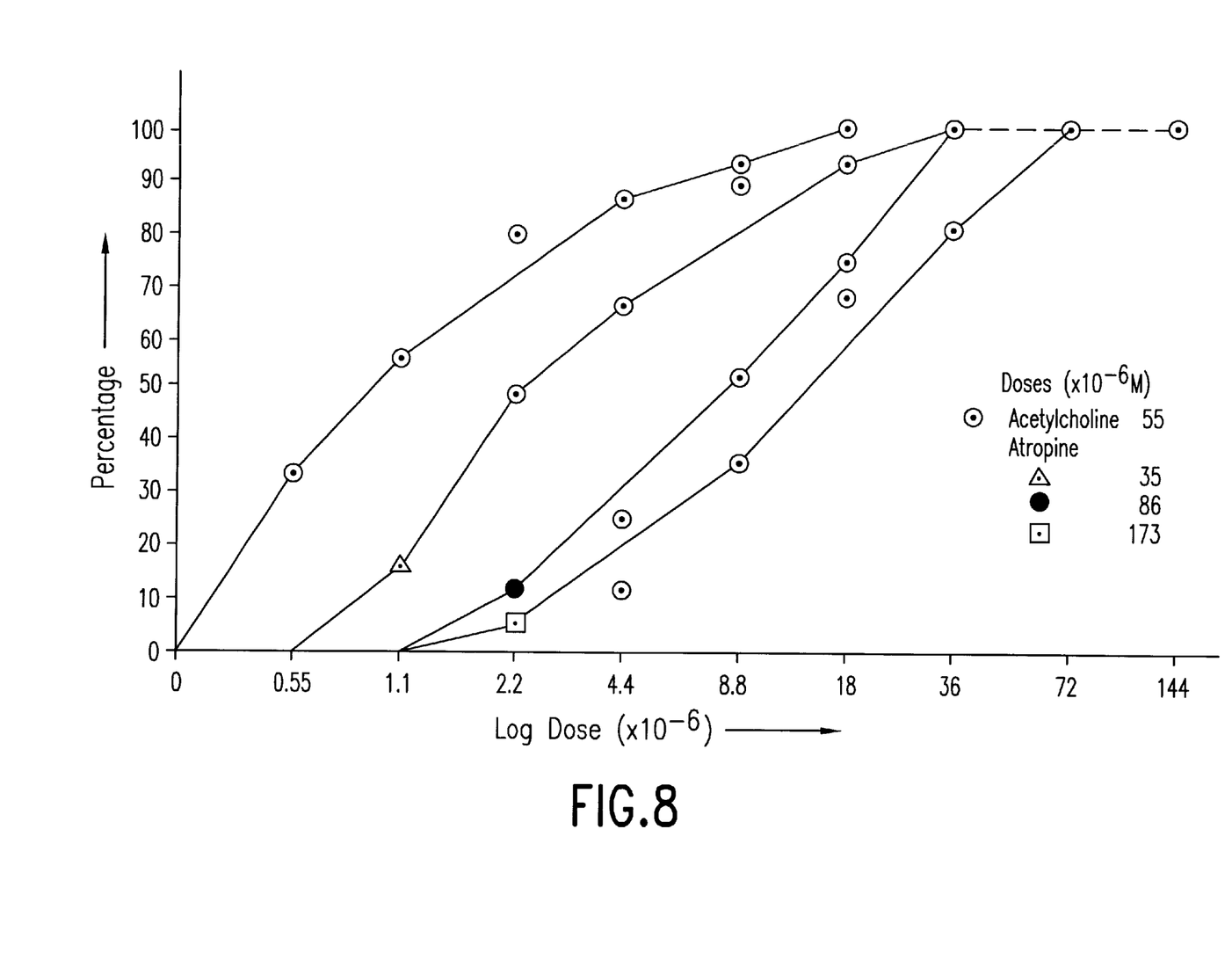
FIG. 8: Dose response curve of acetylcholine on guinea pig bladder in the absence and presence of atropine.

Experiments on the strips of detrusor muscle of the bladder showed that the compound methyl palmitate in concentrations of $98\times10^{-6}$ moles per ml of bath, $196\times10^{-6}$ moles per ml of bath and $392\times10^{-6}$ moles per ml of bath antagonised the effect of acetylcholine in a dose-dependent and competitive manner (FIGS. 7 and 8). The said compound is 2.2 times less potent than atropine.

TABLE 1

Effect of methyl palmitate and atropine on gastric acidity in rats.

| Drug/Compound | Dose (mg/kg s.c.) | % inhibition | $ED_{50}$ (mg/kg) |
|---|---|---|---|
| Control | Saline | | |
| Atropine | 0.01 | 09.00 | 0.055 |
| | 0.05 | 42.00 | |
| | 0.10 | 91.15 | |
| Compound (methyl palmitate) | 1.0 | 50.72 | 02.74 |
| | 3.0 | 55.00 | |
| | 5.0 | 91.50 | |

What is claimed is:

1. A method for mediating gastric secretions and relaxing smooth muscles in a mammal in need thereof comprising administering an effective amount of a muscarine antagonist comprising methyl palmitate obtained from a mangrove plant *Salvadora persica;* wherein said antagonist mediates gastric secretions and relaxes smooth muscle by selectively binding to $M_1$ and $M_3$ receptors, respectively.

2. The method of claim 1, wherein said effective amount is from 0.1 to 10 mg/kg of body weight.

3. The method of claim 1, wherein said antagonist inhibits gastric acidity in stomach muscles by binding to $M_1$ subtype muscarine receptors.

4. The method of claim 1, wherein said antagonist relaxes ileal and bladder detrusor muscles by binding to $M_3$ subtype muscarine receptors.

5. A method of treating muscarine disorders, comprising administering to a person in need thereof an effective amount of a muscarine antagonist having as an active agent methyl palmitate.

6. The method of claim 5, wherein said muscarine disorders are selected from the group consisting of renal colitis, motion sickness, abdominal cramps and bronchial asthma.

7. The method of claim 5, wherein said effective amount is 0.1 to 10 mg/kg of body weight.

8. The method of claim 5, wherein said antagonist binds to $M_1$ and $M_3$ subtype muscarine receptors.

* * * * *